(12) United States Patent
Wellisz et al.

(10) Patent No.: US 6,302,884 B1
(45) Date of Patent: Oct. 16, 2001

(54) BONE ALIGNMENT AND FIXATION DEVICE AND INSTALLATION METHOD

(75) Inventors: Tadeusz Z. Wellisz; Eric V. Hohenstein, both of Los Angeles, CA (US)

(73) Assignee: Bioplate, Inc., Los Angeles, CA (US)

( * ) Notice: Subject to any disclaimer, the term of this patent is extended or adjusted under 35 U.S.C. 154(b) by 0 days.

(21) Appl. No.: 09/669,439

(22) Filed: Sep. 25, 2000

Related U.S. Application Data

(63) Continuation-in-part of application No. 09/435,646, filed on Nov. 9, 1999, now Pat. No. 6,190,389.

(51) Int. Cl.⁷ .................................................. A61B 17/80
(52) U.S. Cl. ................................. 606/69; 606/72; 606/73
(58) Field of Search ........................... 606/69, 70, 72, 606/75, 86, 104, 151; 29/243.56; 411/61, 508

(56) References Cited

U.S. PATENT DOCUMENTS

| 4,936,844 | * | 6/1990 | Chandler et al. | 606/69 |
| 5,674,222 | * | 10/1997 | Berger et al. | 606/69 |
| 5,810,822 | * | 9/1998 | Mortier | 606/69 |
| 5,868,746 | * | 2/1999 | Sarver et al. | 606/69 |
| 5,953,803 | * | 9/1999 | Hahn | 29/243.56 |
| 6,190,389 | * | 2/2001 | Wellisz et al. | 606/69 |

* cited by examiner

Primary Examiner—Pedro Philogene
(74) Attorney, Agent, or Firm—William W. Haefliger

(57) ABSTRACT

This invention concerns a device, and instruments for its insertion, that aligns two sections of bone and fixates the two sections to one another. The alignment feature and the fixation feature are typically independent, but they are incorporated into one device. The device is particularly well adapted to the alignment and fixation of a fragment of cranial bone with the remainder of the cranium. The device can be applied to a cranial bone fragment, and it allows the bone fragment to be aligned with the outer cortex of the cranium; prevents the bone fragment from entering the cranial cavity; and if desired, fixates the bone fragment to the cranium. The device may take the form of a clip having a tab to surface engage one section of bone, two projections to respectively engage edge portions of two bone sections, and an S-shaped flange integral with the tab and at least one of the projections.

58 Claims, 11 Drawing Sheets

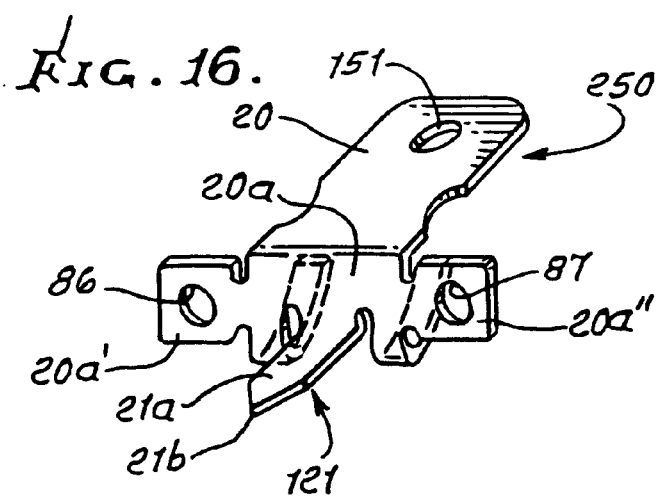
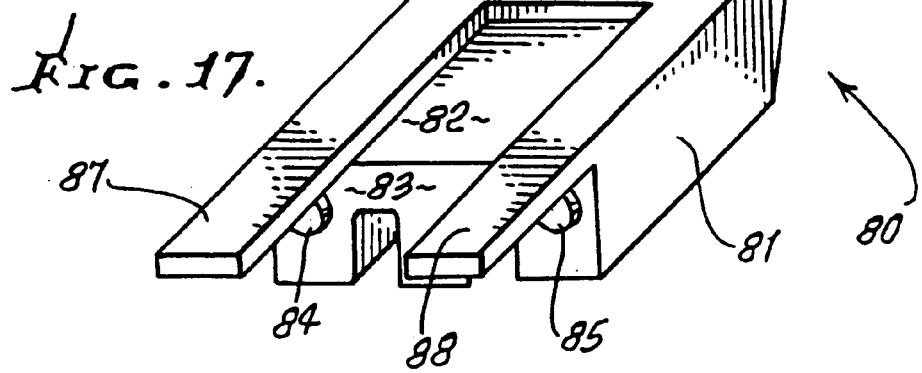
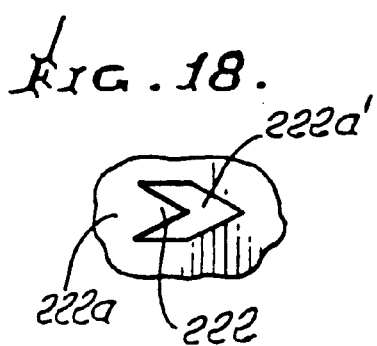
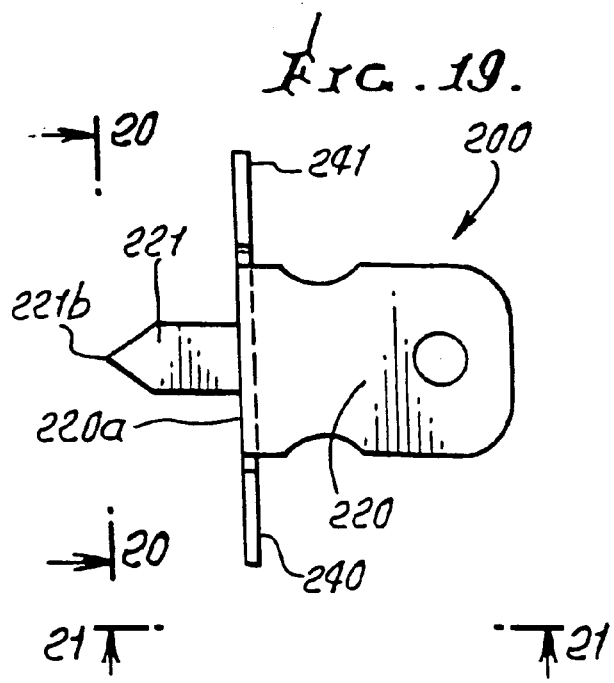

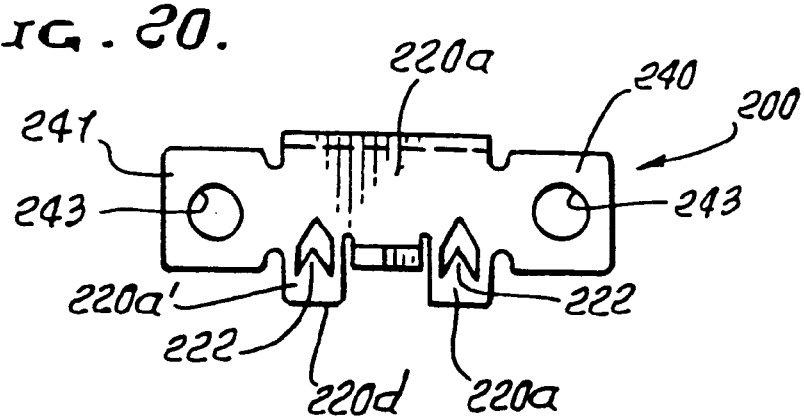
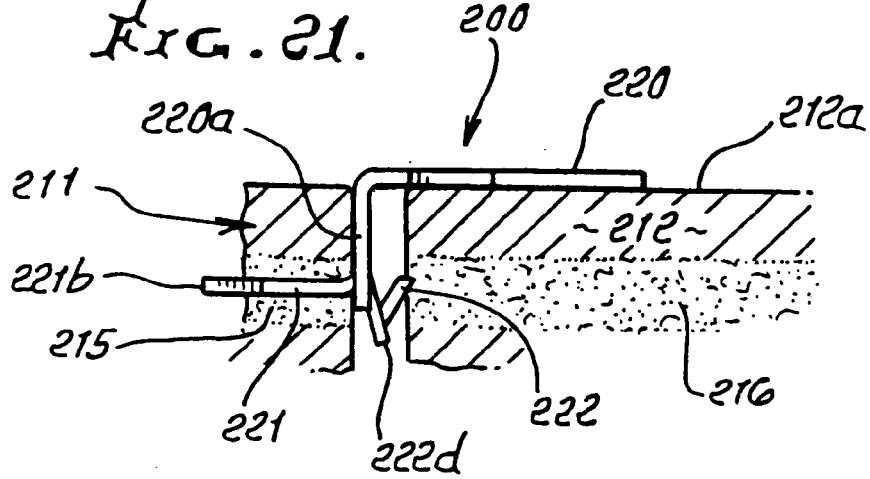
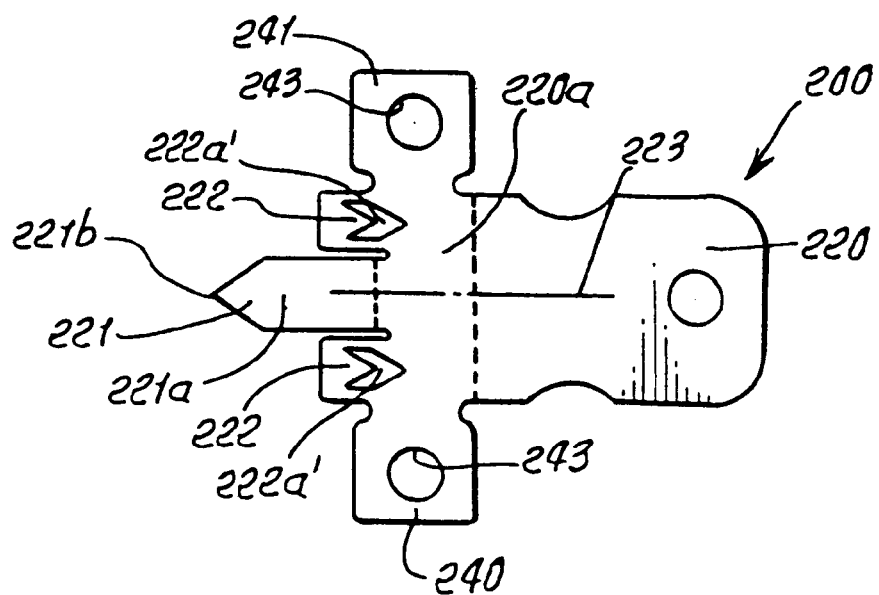

BONE ALIGNMENT AND FIXATION DEVICE AND INSTALLATION METHOD

This application is a continuation-in-part of prior pending U.S. patent application Ser. No. 09/435,646, filed Nov. 9, 1999 now U.S. Pat. No. 6,190,389.

BACKGROUND OF THE INVENTION

This invention relates generally to the alignment and fixation of bone segments as required for appropriate bone healing, for example after fracture or surgical intervention, and specifically to a device, and the tools needed to install the said device, for the alignment and fixation of cranial bone fragments.

In cases of bone fragmentation where bone fixation is desired, the appropriate alignment of the bone is also a desired result. This is especially true in the cranium, where bone fragmentation can occur as a result of trauma, congenital deformity, or of surgical intervention. In the field of neurosurgery, cranial bone fragments are frequently cut and removed to create defects to allow for access into the cranial cavity and the brain.

The bony cranium is generally regarded to have two surfaces: the outer surface which is characterized by the outer cortex of the bone and is adjacent to the scalp and soft tissue; and the inner surface which is characterized by the inner cortex of the bone and which is adjacent to the cranial cavity and the brain. Between the inner cortex and the outer cortex, which are dense layers of bone, lies the diploe which generally consists of soft bone and bone marrow. When a bone fragment is created, a cut between the bone fragment (the primary bone zone) and the remainder of the cranium (the secondary bone zone) is present.

Several methods of alignment and fixation of primary and secondary bone zones are known. Traditional techniques involve the use of several pieces of filament, such as wire, that are tied after being threaded through holes drilled obliquely through the outer cortex to the cut surface of both bone zones. Precise alignment of the two zones can be difficult and the technique can be cumbersome.

Commonly, the zones of bone can be aligned and fixated with a system of plates and screws (U.S. Pat. Nos. 5,372,598; 5,413,577; and 5,578,036). A plate made of metal or other substance can be fixated to the outer cortex of the primary bone zone with screws whose penetration of the bone can be limited to the outer cortex. With three of more plates attached to the primary bone in such a way that the plates protrude beyond the edges of the primary bone zone, the primary bone zone can be introduced into a defect and aligned to the outer cortex of the secondary bone zone without danger of the primary bone zone falling too deeply into the defect in the secondary bone zone and exerting pressure on the underlying tissue such as the brain. Fixation can then be achieved by employing additional screws fixating the plates to the outer cortex of the secondary bone zone. Plates and screws systems allow for the alignment and fixation of the zones, while preventing the primary bone zone from falling below the level of the secondary bone zone without actually introducing a component of the device below the secondary bone zone. A plate with a spring clip extension has been described (U.S. Pat. No. 5,916,217). Plate and screw systems can be expensive and time consuming to use.

Devices that align the two bone zones by way of compressing them between the two disks positioned along the inner and outer cortex have been described. (Foreign Patents: DE 19603887C2, DE 19634699C1, DE 29812988U1, EP 0787466A1.) A pin connects the two disks aligning and securing two bone zones. These devices introduce foreign material that is left below the inner cortex, and they do not protect the underlying tissue from compression during the installation procedure.

Devices that fixate bone zones using friction forces created by a cam without a component that extends below the inner cortex are known and described (Patent DE 19634697C1). These devices also do not protect the brain from compression during the installation procedure.

Intramedulary pins are well known in the orthopedic fields for alignment of long bones. Such pins have also been described for cranial fixation (U.S. Pat. No. 5,501,685); however, the bone zones can not be aligned in three dimensions with this technique.

There is a need for an alignment and fixation device that is simple and rapid to use, versatile, and ultimately cost effective.

OBJECTS OF THE INVENTION

The object of the invention is to provide a device and instruments for its use and installation that aligns one cortex of a primary zone with one cortex of a secondary bone zone without extending to the opposing cortex, and which accurately fixates the bone zones to each other. When used in the field of neurosurgery, the device is applied to the primary bone zone and it aligns the outer cortex of the primary bone zone with the outer cortex of the secondary bone zone; it prevents the primary bone zone from entering the cranial cavity; and it provides fixation of the two bone zones. The alignment feature can be used independently from the fixation feature. An example of the use of the alignment feature is in the replacement of a cranial bone fragment which will be held in place by the tissue forces of the scalp, which allows for the bone fragment to be elevated away from the cranial cavity in cases where brain swelling occurs. Fixation can also be applied to attach the alignment device to the bone, using elements alone or in combination such as filaments, screws, rivets, pins, clips, cams, friction or adhesives. The alignment aspect of the invention can also be applied to situations where it is desired to offset the alignment of the bone fragment to the adjacent bone such as where the object is to create a more prominent chin by cutting the bone of the chin and advancing the bone fragment.

The fixation feature of the invention is likewise independent from the alignment feature. The fixation feature of the device relies on the principle that the device is fixated to the primary bone zone and the fixation feature grips the secondary bone zone by means of spring loaded tab or hook elements engaging the soft areas of the medullary space, irregularities along the cut surface, or a slot cut into the cut surface of the secondary bone zone.

SUMMARY OF THE INVENTION

The invention provides an improved clip meeting the above need or needs.

As will be seen the preferred clip is configured to interconnect primary and secondary bone zones having edges spaced apart by a gap, the clip comprising a) a tab such as a small plate to extend over and generally parallel to a surface of the secondary bone zone, and above a first level defined by that surface, and b) a first projection carried by the tab and configured to penetrate the primary bone zone at the edge thereof, and below said surface level.

As will be seen, a second projection may be provided and carried by the tab and configured to engage the secondary bone zone at the edge thereof, and below said surface level.

It is another object to provide an extension of the tab projecting below said first level. That extension may carry the first projection, and may carry the second projection, if it is provided. In this regard, the second projection is typically located beneath the tab; and the first projection extends generally parallel to the tab and forwardly from a part of the tab extension below said surface level, and it preferably has a sharp terminal to enable penetration of diploe.

A further object is to provide the second projection to have a sharp terminal, and to extend at an angle toward the tab, in order to resist removal relative to the secondary bone zone.

Yet another object is to provide another second projection carried by the tab in sidewardly spaced relation to the first mentioned second projection, and configured to engage the secondary bone zone at the edge thereof, and below said surface level.

An additional object is to provide a tab extension as referred to, but having S-shape or configuration, whereby enhanced spring support of one or both projections is realized; and also the S-shape of the extension facilitates its formation or manufacture.

An additional object is to provide a plate or flap defining the primary bone zone, and to provide multiple of the clips having their first projections penetrating the primary bone zone at different edges thereof, below a surface defined by the plate or flap.

The method of using the clip as referred to includes the steps i) advancing the first projection to penetrate the primary bone zone, ii) and locating the tab to extend over the surface of the secondary bone zone, and attaching the tab to that surface.

As will be seen, the step i) preferably includes pushing the clip toward the primary bone zone to effect push-in penetration of the first projection into the primary bone zone. The method may further include providing a second projection carried by the tab and configured to engage the secondary bone zone at the edge thereof, and below its top surface level, the method including displacing the clip and said second projection to engage the secondary bone zone at the edge thereof, below said surface level. An additional step includes displacing the clip in a direction to effect scraping of the edge of the secondary bone zone by the second projection, the second projection oriented to resist reverse displacement of the clip in an upward or opposite direction relative to the secondary bone zone. In this regard, the method may include effecting penetration of the edge of the secondary bone zone by the second projection in an angular direction toward the tab. The bowed or S-shape of the extension provides enhanced spring effect to aid in effecting such penetration.

These and other objects and advantages of the invention, as well as the details of an illustrative embodiment, will be more fully understood from the following specification and drawings, in which:

DRAWING DESCRIPTION

FIG. 16 is a perspective view of a further modified clip, of FIG. 2 type;

FIG. 17 is a perspective view of a tool usable in conjunction with the FIG. 16 clip, to effect penetration of a clip projection into a primary bone zone;

FIG. 18 shows use of a barb;

FIG. 19 is a top plan view of a further modified clip using a barb;

FIG. 20 is an end view taken on lines 20—20 of FIG. 19;

FIG. 21 is a side elevational view taken on lines 21—21 of FIG. 19;

FIG. 22 is a plan view of a clip blank in one plane, prior to deformation to FIG. 19 configuration;

DETAILED DESCRIPTION

Figure 1:
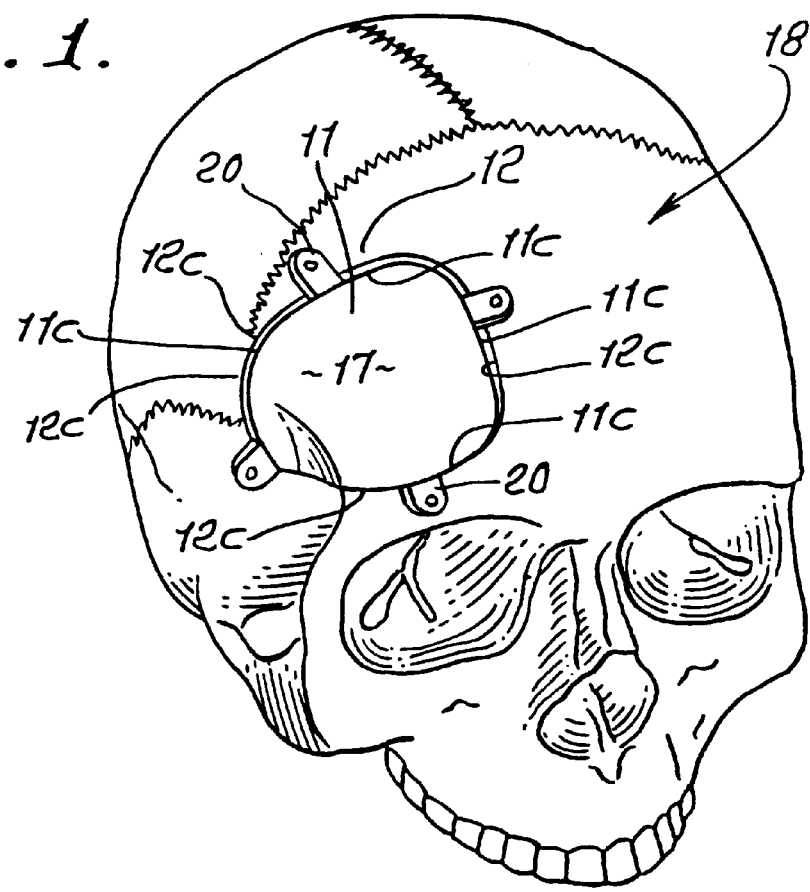
FIG. 1 is a perspective view showing a bone flap fixated on a skull, employing fixation clips.
Figure 2:
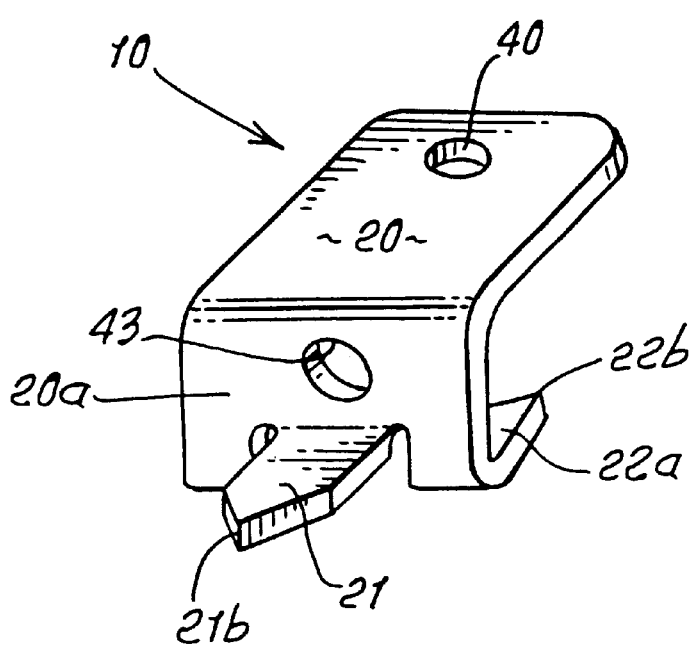
FIG. 2 is an enlarged perspective view showing a clip employing the invention.

Referring to FIGS. 2–5 and 7, the illustrated clip 10 is configured to interconnect primary and secondary bone zones 11 and 12 having opposed and spaced apart edges 11c and 12c. A cut or gap 13 is formed between the opposed edges of the primary and secondary bone zones. Diploe is shown at 15 between the top and bottom surfaces 11a and 11b of zone 11; and at 16 between the top and bottom surfaces 12a and 12b of zone 12. As also seen in FIG. 1, primary bone zones 11 may be defined by bone flap 17; and secondary bone zones 12 may be defined by skull 18 and its zone extents at 12 opposing zones 11. In the adult, cranial bone or skull averages 7 mm in thickness, but varies between 3 and 12 mm.

The clip 10, which is preferably metallic includes the following a) a tab 20 to extend over a surface 12a of the secondary bone zone 12, above surface level and generally parallel to surface 12a;

b) a first projection 21 carried by the tab and configured to penetrate the exposed diploe of the primary bone zone 11 at the edge 11c of that zone (and typically into diploe 15);

c) and at least one second projection 22 carried by the tab and configured to engage (for example gouge into) the exposed diploe of the secondary bone zone 12 at its edge 12c, below the level of surface 12a.

Figure 4:
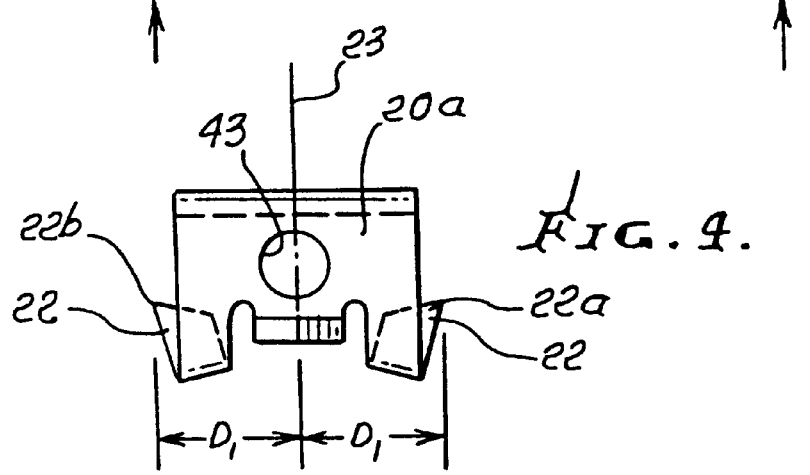
FIG. 4 is an end view of the clip taken on lines 4—4 of FIG. 3.
Figure 5:
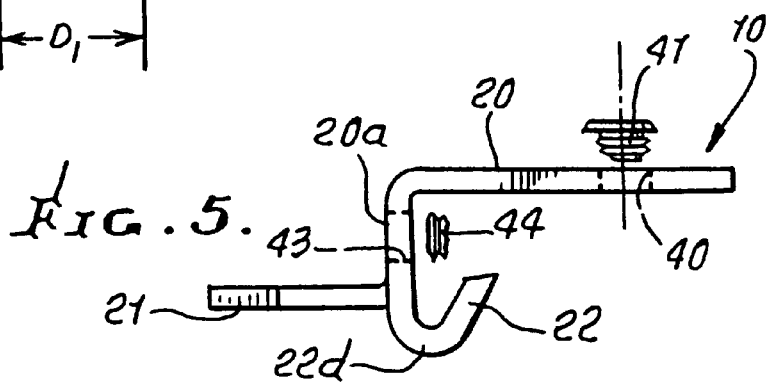
FIG. 5 is a side elevational view taken on lines 5—5 of FIG. 3.
Figure 6:
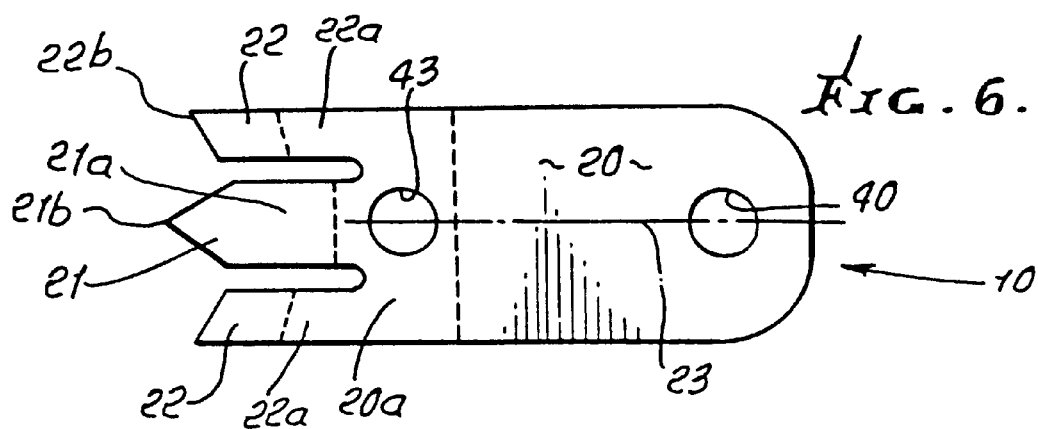
FIG. 6 is a plan view of a clip blank in one plane, prior to deformation to FIG. 2 configuration.
Figure 7:
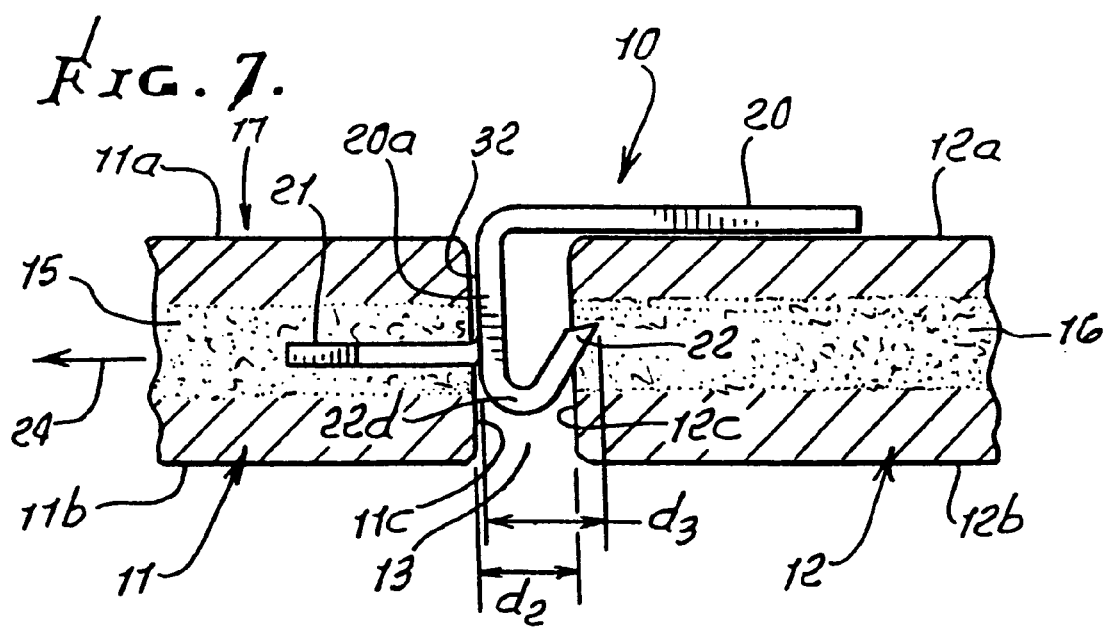
FIG. 7 is a section showing the FIG. 1 clip attached to primary and secondary bone zones.
Figure 9:
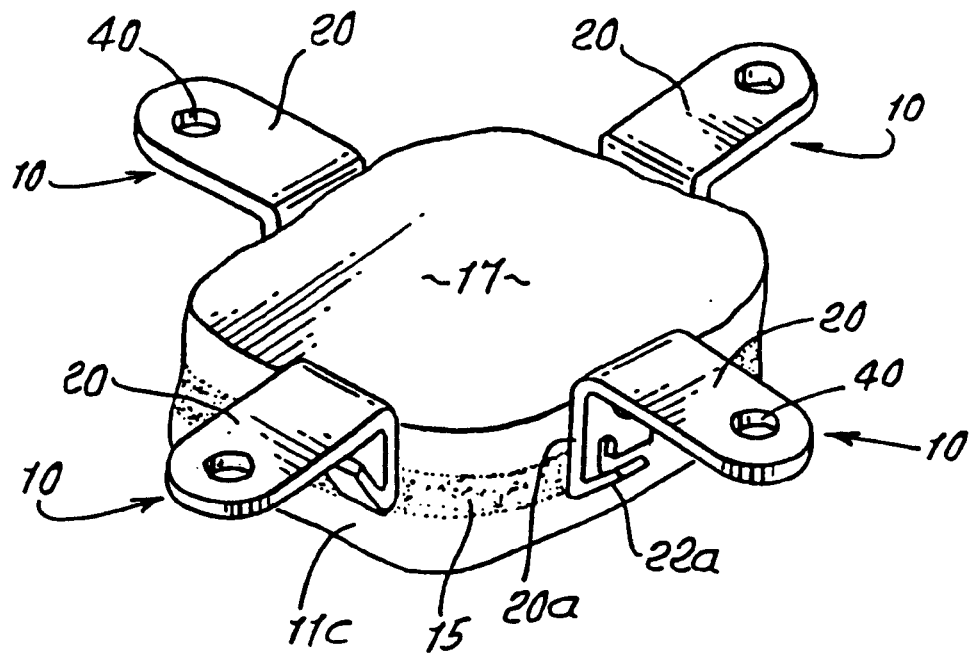
FIG. 9 shows multiple clips attached to opposite edges of a bone flap defining primary bone zones.

In the example, two such second projections are provided, as is clear from FIGS. 4 and 6, and they are located at opposite sides of a lengthwise plane 23 bisecting the clip, including projection 21. See FIGS. 4 and 6. Such projections are equally spaced from plane 23, as indicated by dimensions $D_1$, seen in FIG. 4. The projections 21 and 22 have legs 21a and 22a, and their terminals are sharpened at 21b and 22b, to facilitate penetration of the diploe zones, as seen in FIG. 7. Leg 21a and projection 21 extend forwardly in direction 24 from a tab downward extension 20a; and projection 22 extends back upwardly at an approximate angle of 30° toward the underside of the tab 20. Note that leg 22a extends from tab extension 20a and is U-shaped. A bend is formed at 22d. Projections 22 may also diverge laterally oppositely, as seen in FIG. 4, to provide greater stability of the plate or flap 17, as in FIG. 10 installed condition. Four edges 11c of that flap are seen in FIGS. 1 and 9, and corresponding four edges 12c of the skull face the flap edges and receive penetration of the stabilizing clip projections 22, as described.

The method of use of the clip or clips includes the following steps:

i) causing the first projection or projections 21 to penetrate the primary bone zone or zones;

ii) and then causing the second projection or projections 22 to grip the secondary bone zone at the edge thereof.

Figure 8:
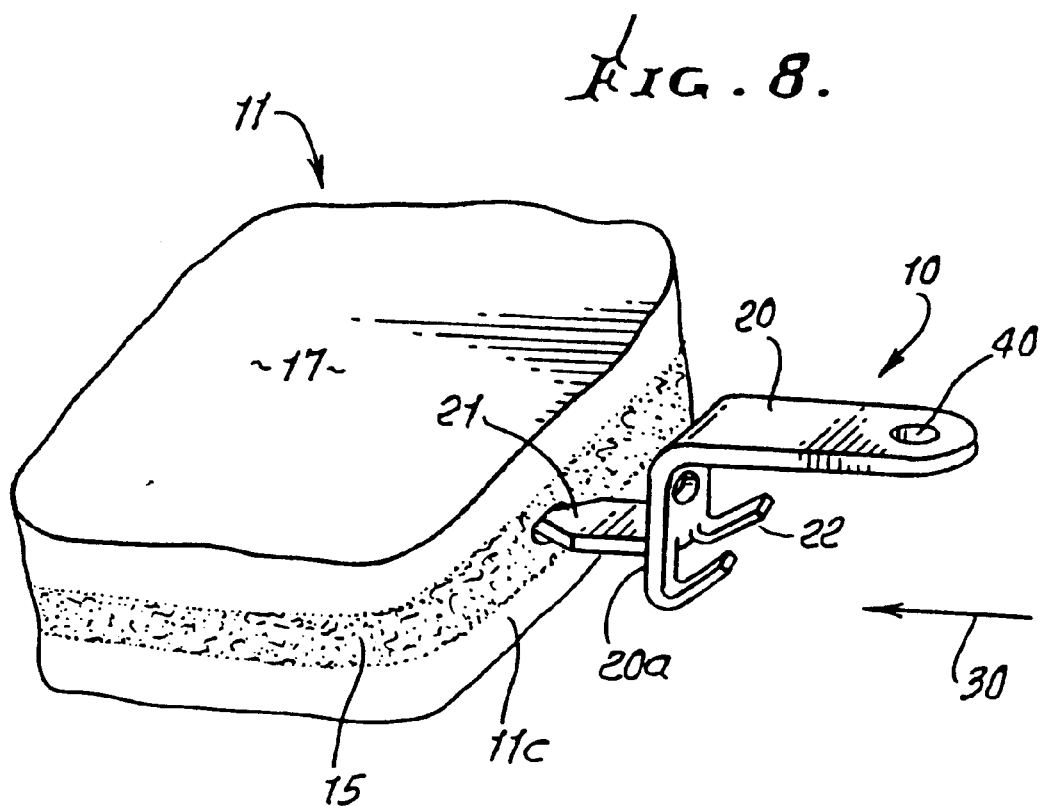
FIG. 8 is a perspective view showing clip attachment to a primary bone zone.

Step i) includes pushing the clip 10 relatively toward the edge 11c of the primary bone zone 11, as in direction 30 seen in FIG. 8. This effects push-in penetration of the first projection 21 into the bone zone 11, as for example into diploe 15. Push-in is typically completed when bent down tab extension 20a closely approaches and/or engages edge 11c of the primary bone zone 11 defined by the plate or flap 17. Four such pushed-in clips are seen in FIG. 9, the clips located in opposed pair positions, at four sides of the flap 17. Each tab 20 has a through hole 40 drilled or formed therein to receive a fastener such as a retention screw, indicated at 41 in FIG. 5, to penetrate and attach to the skull proximate the secondary bone regions.

The step ii) preferably also includes displacing the clip in a direction (typically relatively downwardly toward the skull to bring 21, 22, and 20a into gap 13 as seen in FIG. 7) to effect scraping of the edge 12c of the secondary bone zone 12 by the tip of the angled second projection. That projection is oriented, i.e. angled, to resist displacement of the clip in an upward or opposite direction, relative to bone zone 12. For example, attempted upward and outward displacement would increase the "gouge-in" movement of the second projection, into the diploe 16.

Note further that the installed spacing $d_2$ of the bone zone edges 11c and 12c is slightly less than the spacing $d_3$ as measured from the sharp terminal of the projection 22 to the surface 32 of the tab extension facing the edge 11c. The width $d_2$ of gap 13 between 11c and 12c is slightly less than the dimension $d_3$, i.e.

$$d_2 < d_3,$$

to provide a desirably tight installation of plate 17 into the corresponding skull opening.

Figure 3:
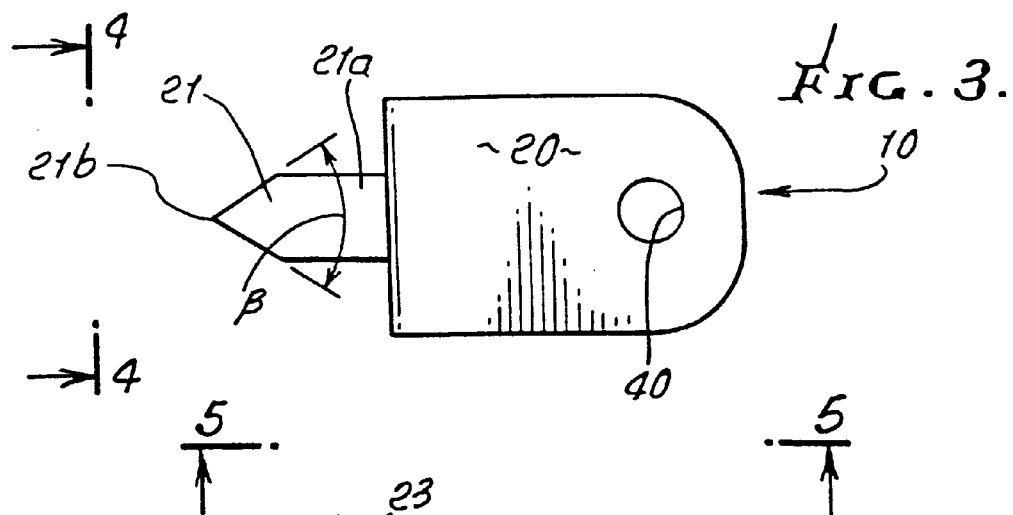
FIG. 3 is a top plan view of the FIG. 2 clip.

In FIG. 3 note angularity β of the sharpened taper of projection 21, where β is approximately 67°, and the through opening 43 in tab extension 20a to receive a fastener 44 (if used to attach extension 20a to 11.

Figure 10:
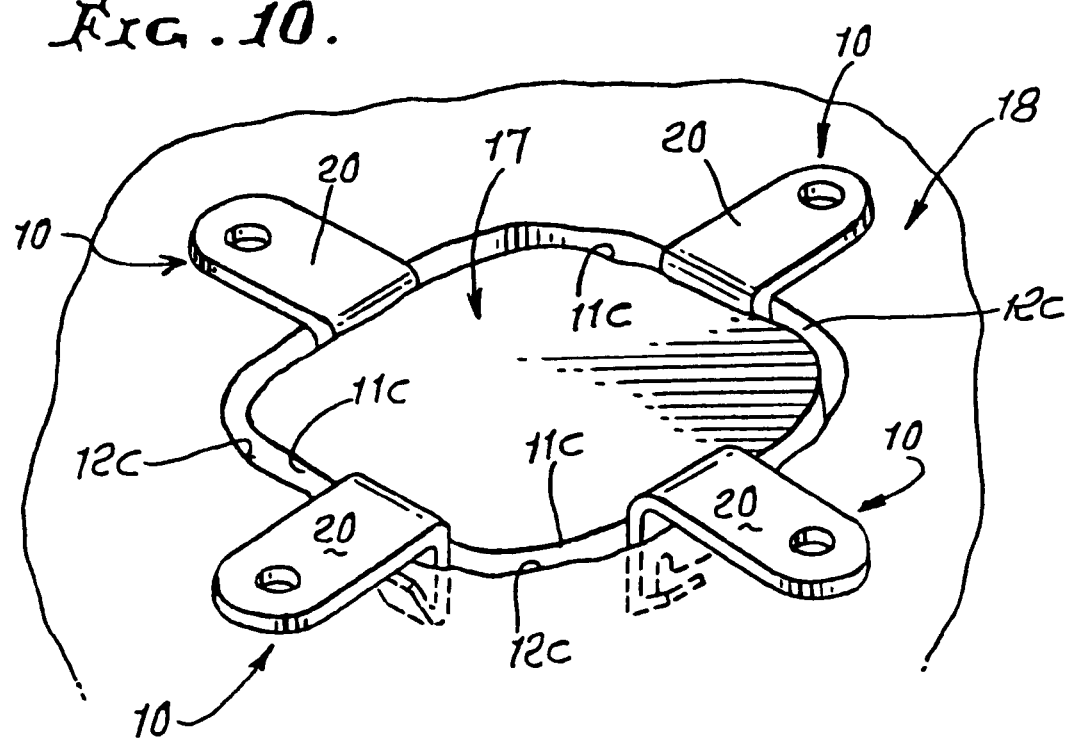
FIG. 10 shows the clips installed in a skull opening.

Projections 22 can resiliently deflect, slightly to accommodate the multiple clips to the gaps 13 between 11 and 12, as during plate or tab downward installation, as seen in FIG. 10.

Figure 11:
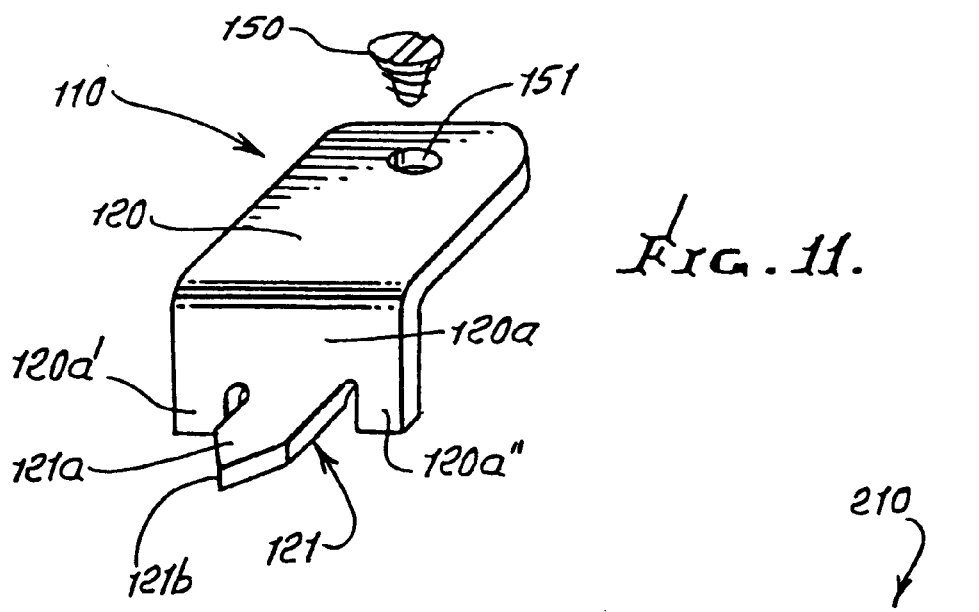
FIG. 11 is a perspective view like FIG. 2, showing a modified clip.
Figure 14:
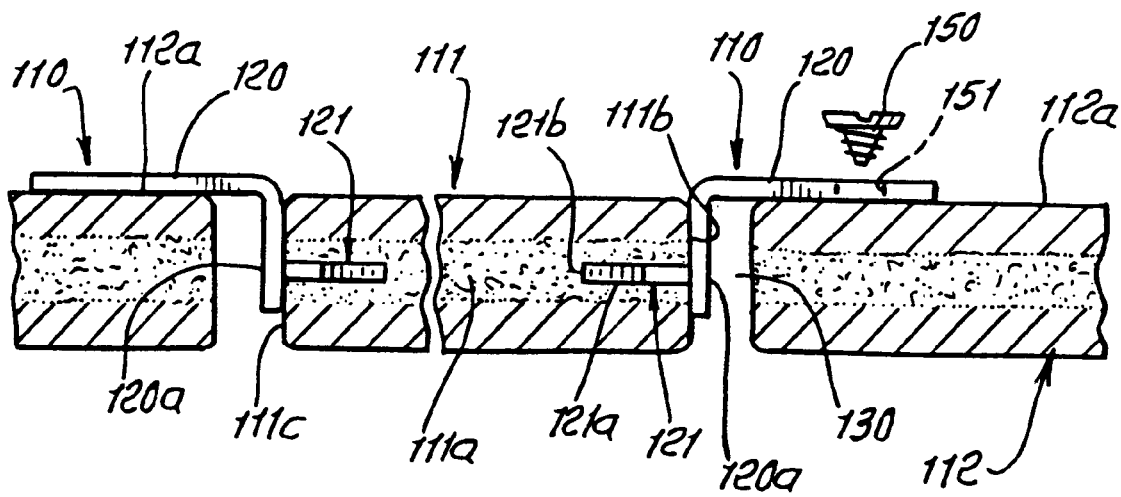
FIG. 14 is a section taken through a cranial bone flap, having two FIG. 11 type clips attached at opposite edges, and positioned for clip attachment to secondary bone zone sections.

Reference is now made to the modified clip 110 of FIGS. 11 and 14. It includes:

a) a tab or plate 120 to extend over a surface 112a of secondary bone zone or zones 112 (see FIG. 14), above a level defined by that surface; and b) a first projection 121 carried by the tab 120, and configured to penetrate the edge of exposed diploe 111a of primary bone zone 111, below the levels of tab 120 and surface 112a.

Figure 13:
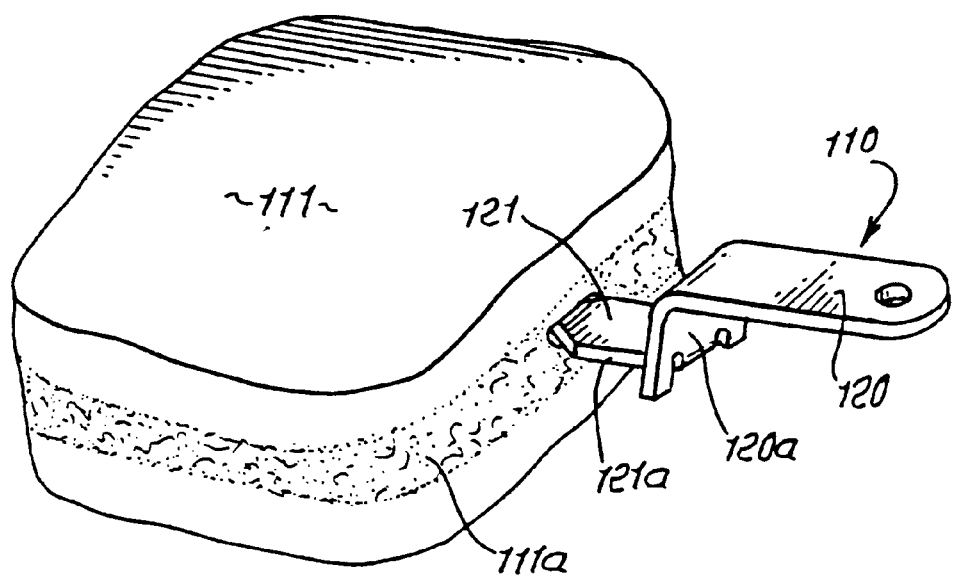
FIG. 13 is a perspective view similar to FIG. 8, and showing attachment of a clip of FIG. 11 form, to a primary bone zone, such as a bone flap.

The projection or tang 121 has a leg 121a, and its forward terminal is sharpened at 121b to facilitate penetration into the bone marrow zone, as seen in FIG. 14. Leg 121a extends forwardly from a tab downward extension 120a in the form of a flange. The method of use of the clip 110 includes the following steps:

i) causing the projection 121 to penetrate the primary bone zone, such as into diploe, (see FIG. 13); and ii) locating the tab 120 to extend over the surface 112a of the secondary bone zone, as in FIG. 14 for example, and attaching the tab to that surface, one mode of attachment being by use of a screw seen at 150 in FIG. 14, to penetrate through a hole 151 in tab 120, and into secondary bone zone 112.

Figure 15:
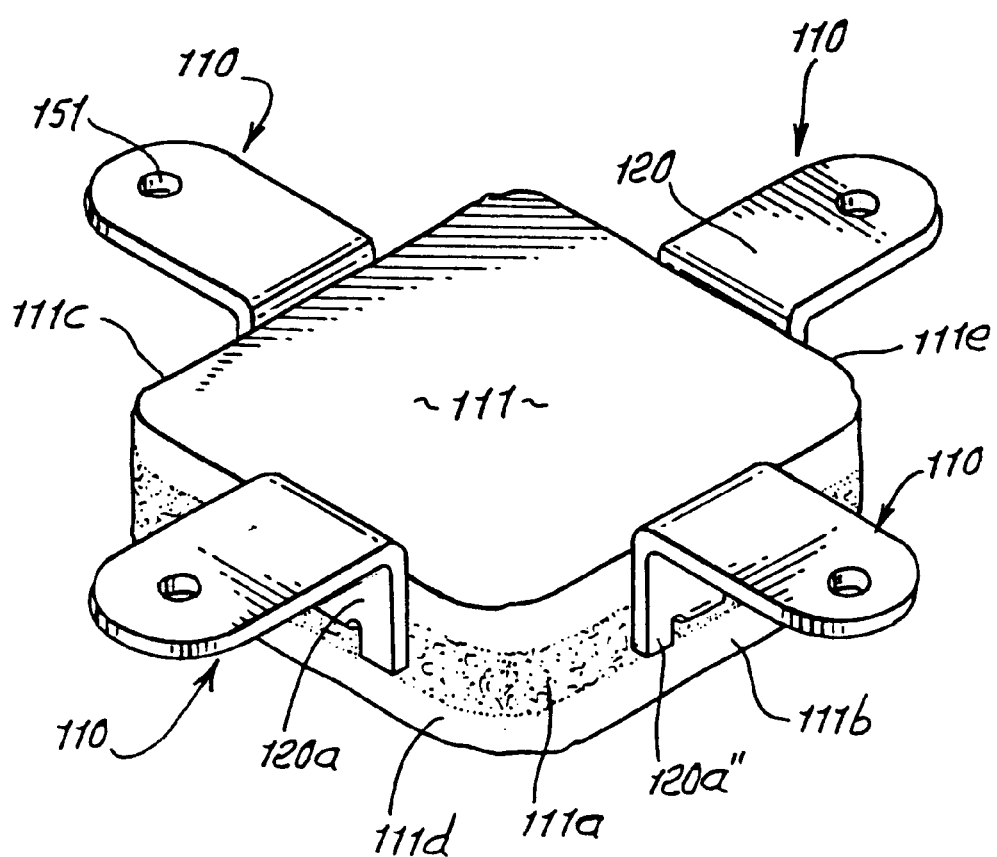
FIG. 15 is a perspective view showing a cranial bone flap having four FIG. 11 type clips attached, at its four edges.

FIG. 14 shows two such clips 110 attached to opposite edges 111b and 111c of a primary bone zone 111, such as a flap removed from the skull. When the flap is attached to the skull, as into opening 130, the tabs 120 are attached to the upper surfaces 112a of the skull, at opposite sides of the opening. FIG. 15 shows four such clips attached to the flap 111, at four edges 111b–111e.

Figure 12:
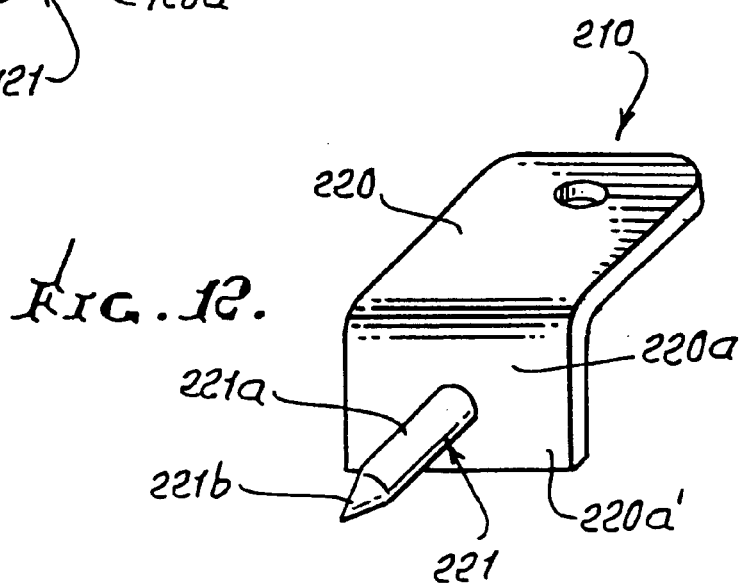
FIG. 12 is a perspective view like FIG. 11 showing another modified clip.

FIG. 12 illustrates a modified clip 210, having elements 220, 220a, 221, 221a and 221b, like corresponding elements of clip 110. Extension 120a in FIG. 11 has two laterally spaced legs 120a′ and 120a″ that extend downwardly below the level of projection 121, and projection 121 has flat upper and lower surfaces; whereas in FIG. 12 the extension lower extent 220a′ is laterally continuous, and projection 221 is cylindrical, and tapers at its forward end.

A further modified clip 250 is shown in FIG. 16, and has elements like those of clip 10, as viewed in FIGS. 2–7. Such corresponding elements are given the same numbers. Also, the clip downward extension 20a has left and right wings 20a′ and 20a′.

FIG. 17 shows a hand tool 80 to receive the FIG. 16 clip in position for forward, push-in attachment to bone zone 11, as described. Tool 80 has a body 81, with a top recess 82 to fit the tab 20. Forward facing surface 83 engages and positions the clip downward extensions 20a and its two wings 20*a*′ and 20*b*′. Tool pins 84 and 85 closely fit into holes 86 and 87 in those two wings, for alignment. Aligners in the form of alignment bars 87 and 88 projecting forwardly from body 81 ride onto the top surface 11*a* of the flap 11, prior to penetration of the projection 21*a* into the marrow 15, so that the proper level of the projection 21 relative to top surface 11*a* is selectively established by operation of the aligners. A tool handle appears at 89, and facilitates forward pushing of the tool and clip, and retraction of the tool, off the clip after its push-in assembly to the flap. In this way, accurate assembly is rapidly achieved.

The clips as disclosed herein may consist of metal or plastic (synthetic resin) material. One desirable metal is titanium.

Clips 10, 110, and 210 may be inverted, for alternate installations relative to the bone zones.

Referring to FIGS. 19–22, the illustrated views of modified clip 200 correspond to views 3–6 of clip 10.

The clip 200, which is preferably metallic, includes the following:

a) a tab 220 to extend over a surface 212*a* of the secondary bone zone 212 above surface level;

b) a first projection 221 carried by the tab and configured to penetrate the exposed diploe of the primary bone zone 211 at the edge 11*c* of that zone (and typically into diploe 215);

c) and at least one second projection such as barb 222 carried by the tab and configured to engage (for example gouge into) the exposed diploe 216 of the secondary bone zone 212, below the level of surface 212*a*.

In the example, two such second projections or barbs 222 are provided, as is clear from FIGS. 20 and 22, and they are located at opposite sides of a lengthwise plane 223 bisecting the clip, including projection 221. One such barb is seen in FIG. 18. Such projections are equally spaced from plane 223, and are formed in lower portions 222*a* of 220*a*, with adjacent through openings 222*a*′. The projection 221 has a leg 221*a*, and its terminal is sharpened at 221*b*, to facilitate penetration of the bone zone 215, as seen in FIG. 21. Leg 221*a* and projection 221 extend forwardly from a tab downward extension 220*a*; and projection or barb 222 extends back upwardly at an acute toward the underside of the tab 220. Note that projection 222 extends from tab lower extension 220*a* and is U-shaped. A bend is formed at 222*d*.

Side wings 240 and 241 integral with downward extension 220*a* contain through openings 243 to receive fasteners (if used) to attach to 221.

Referring to FIGS. 23–27, the illustrated and preferred clip 310 is configured to interconnect primary and secondary bone zones 311 and 312 having opposed and spaced apart edges 311*c* and 312*c*. A cut or gap 313 is formed between the opposed edges of the primary and secondary bone zones. Diploe is shown at 315 between the top and bottom surfaces 311*a* and 311*b* of zone 311; and at 316 between the top and bottom surfaces 312*a* and 312*b* of zone 312. As also seen in FIG. 1, primary bone zones 11 may be defined by bone flap 17; and secondary bone zones 12 may be defined by skull 18 and its zone extents at 12 opposing zones 11. In the adult, cranial bone or skull averages 7 mm in thickness, but varies between 3 and 12 mm.

The clip 310, which is preferably metallic includes the following a) a tab 320 to extend over and generally parallel to a surface 312*a* of the secondary bone zone 312, above surface level;

b) a first projection or tang 321 directly or indirectly carried by the tab and configured to penetrate the exposed diploe of the primary bone zone 311 at the edge 311*c* of that zone (and typically into diploe 315); and wherein the tang 321 may have barbed edges at 321*d* and 321*e*;

c) and at least one second projection 322 carried by the tab and configured to engage (for example gouge into) the exposed diploe of the secondary bone zone 312 at its edge 312*c*, below the level of surface 312*a*.

Figure 23:
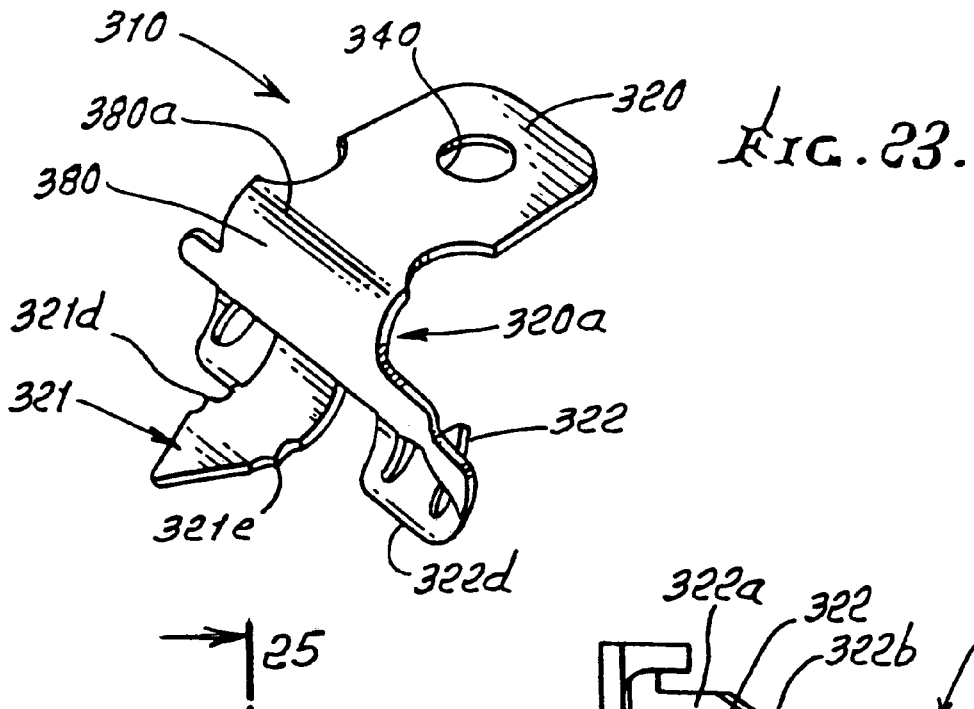
FIG. 23 is a perspective view of a modified clip, of the type shown in FIG. 16.
Figure 24:
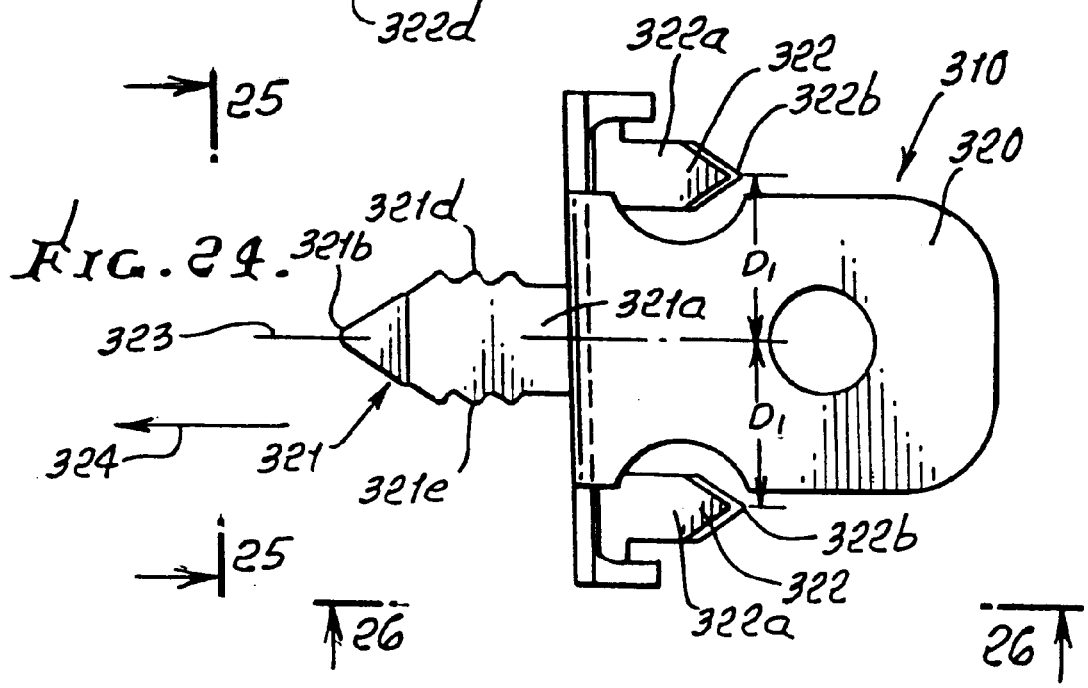
FIG. 24 is a top plan view of the FIG. 23 clip.
Figure 25:
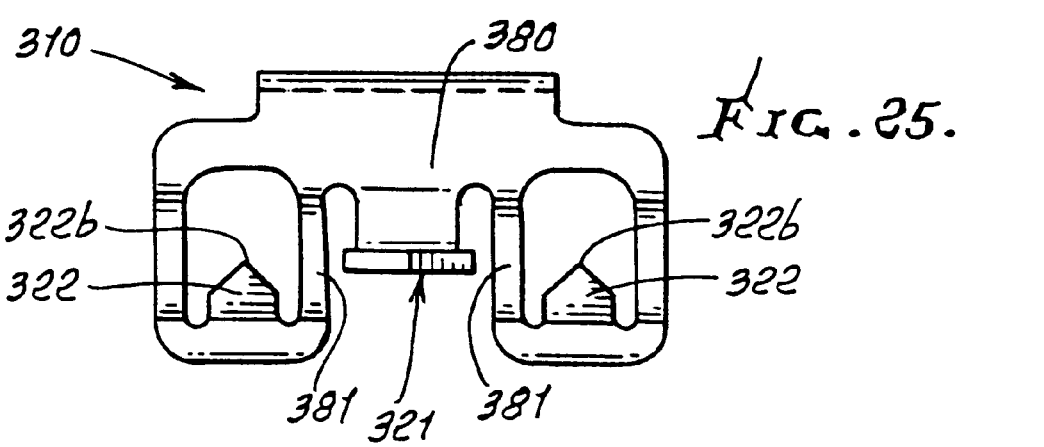
FIG. 25 is a front elevation view of the FIG. 24 clip, and taken on lines 25—25 of FIG. 24.
Figure 26:
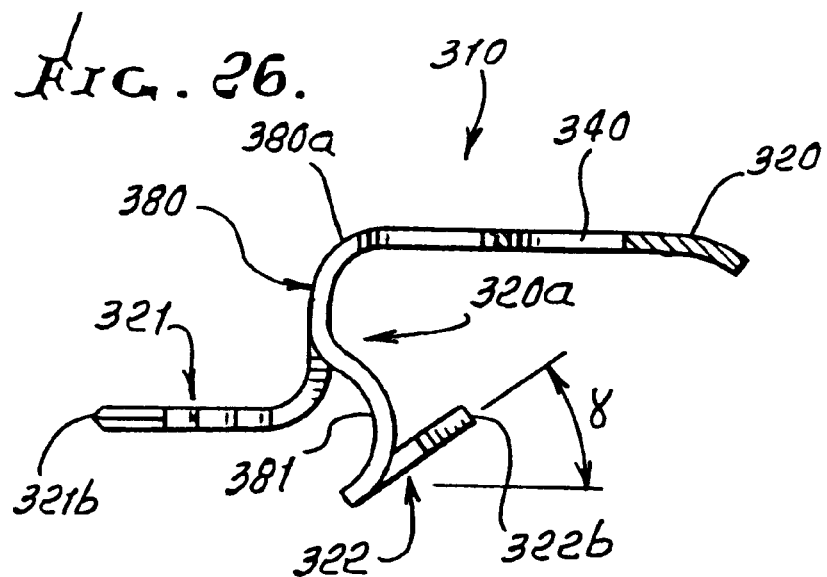
FIG. 26 is a right side elevation taken on lines 26—26 of FIG. 24.

In the example, two such second projections are provided, as is clear from FIGS. 23–25, and they are located at opposite sides of a lengthwise plane 323 bisecting the clip, including projection 321. Such projections are equally spaced from plane 323, as indicated by dimensions $D_1$, seen in FIG. 24. The projections 321 and 322 have legs 321*a* and 322*a*, and their terminals are sharpened at 321*b* and 322*b*, to facilitate penetration of the diploe zones, as seen in FIG. 7. Leg 321*a* and projection 321 extend forwardly in direction 324 from a tab downward extension 320*a*; and projections 322 extend back upwardly at an angle γ between 25° and 45° toward the underside of the tab 320. Note that each projection 322 extends from tab ring-shaped extension 320*a* and is U-shaped. A bend is formed at 322*d*.

Four edges 11*c* of the flap 17 are seen in FIGS. 1 and 9, and corresponding four edges 12*c* of the skull face the flap edges and receive penetration of the stabilizing clip projections 22 or 322, as described.

It will be noted that the generally upright extension 320*a* is bowed to produce an enhanced spring effect for urging one or more of the projections, and also to facilitate ease of manufacture. See extension sections 380 and 381, the former bowed frontwardly in the direction of projection 321; and the latter section 381 bowed in the general direction of the projections 322 extents. Section 380 is curved at 380*a* to merge with the tab. Projection 321 is carried by section 380, and projections 322 are carried by section or sections 381, whereby movements of the projections 322 are isolated from movements of the projection 321, enhancing completeness and permanence of fastening to bone. See for example FIG. 25, showing such isolation.

The method of use of the clip or clips includes the following steps:

i) causing the first projection or projections 321 to penetrate the primary bone zone or zones;

ii) and causing the second projection or projections 322 to grip the secondary bone zone at the edge thereof.

Figure 27:
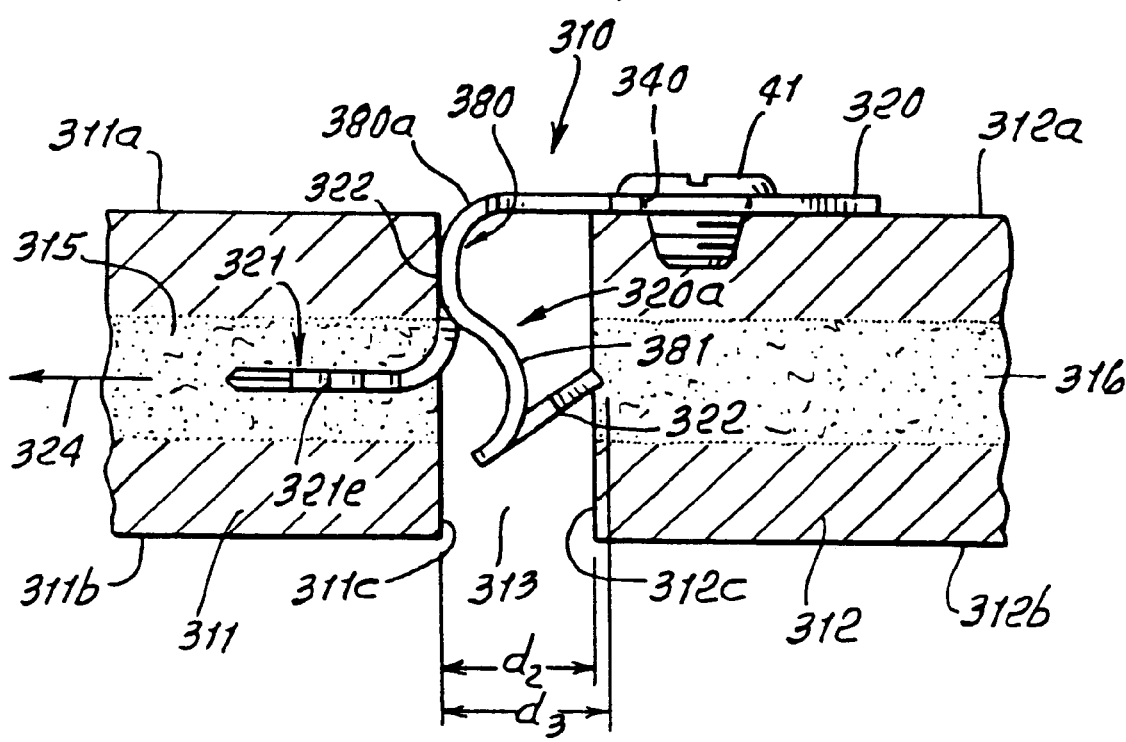
FIG. 27 is a view like FIG. 26, but showing use of the clip of FIGS. 23–26, in the manner of FIG. 21.

Step i) includes pushing the clip 310 relatively toward the edge 311*c* of the primary bone zone 311, as in direction 324 seen in FIG. 27. This effects push-in penetration of the first projection 321 into the bone zone 11, as for example into diploe 15. Push-in is typically completed when bent-down and bowed tab extension 380 closely approaches and/or engages edge 311*c* of the primary bone zone 311 defined by the plate or flap 17 (or bone zone 311). As described above, four pushed-in clips are seen in FIG. 9, the clips located in opposed pair positions, at four sides of the flap 17. Each tab 320 has a through hole 340 drilled or formed therein to receive a fastener such as a retention screw, indicated at 41 in FIG. 5 and also in FIG. 27, to penetrate and attach to the skull proximate the secondary bone regions.

The step ii) preferably also includes displacing the clip in a direction (typically relatively downwardly toward the skull to bring 322, and 320*a* into gap 313 as seen in FIG. 27) to effect scraping of the edge 312*c* of the secondary bone zone 312 by the tip or tips of the angled second projection or projections. Projection or projections 322 is or are oriented, i.e. angled, to resist displacement of the clip in an upward or opposite direction, relative to bone zone 12. For example, attempted upward and outward displacement would increase the "gouge-in" movement of the second projection, into the diploe 16.

As described above, the installed spacing $d_2$ of the bone zone edges 11c and 12c is slightly less than the spacing $d_3$ as measured from the sharp terminal of the projection 322 to the surface 332 of the tab extension facing the edge 311c. The width $d_2$ of gap 13 between 311c and 312c is slightly less than the dimension $d_3$, i.e.

$$d_2 < d_3,$$

to provide a desirably tight installation of plate 17 into the corresponding skull opening.

Projections 322 can resiliently deflect, as by spring bending of sections 381, to accommodate the multiple clips to the gaps 13 between 11 and 12, as during plate or tab downward installation, as seen in FIG. 10. In FIG. 25, the lateral spacing of bowed sections 381 enhances clip installed stability.

Figure 28:
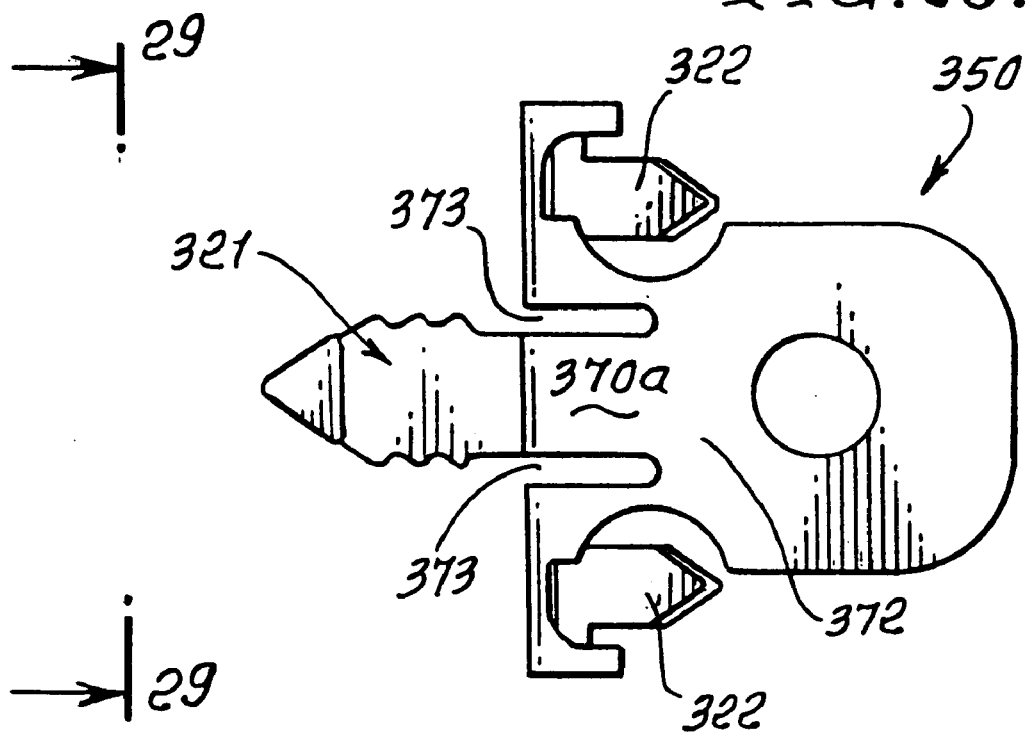
FIG. 28 is a view like FIG. 24, but showing a further modification.
Figure 29:
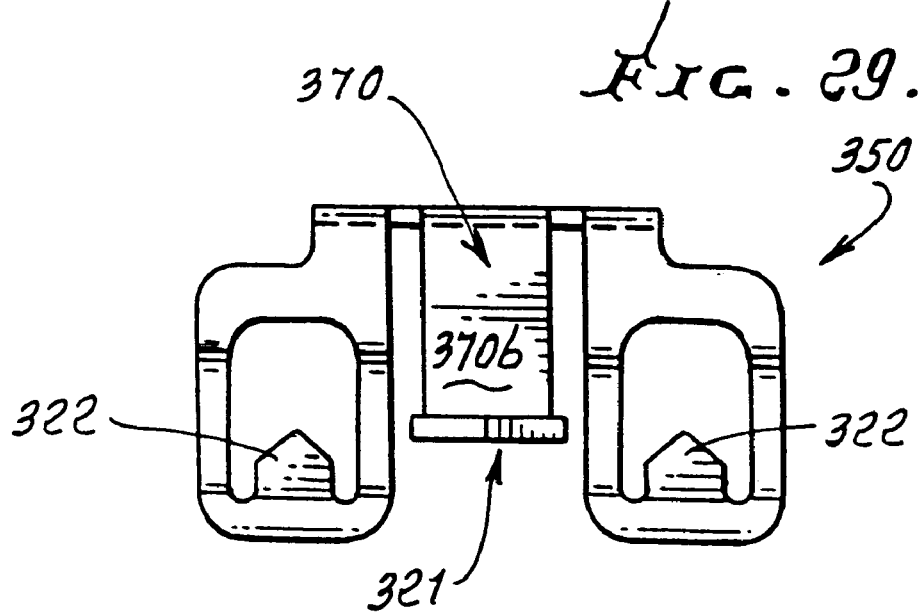
FIG. 29 is a front elevation of the FIG. 28 modified clip, taken on lines 29—29 of FIG. 28.

Reference is now made to FIGS. 28 and 29 showing a clip 350 like clip 310; except that projection 321 is carried by an L-shaped arm 370 having horizontal and vertical extents 370a and 370b. The former extent 370a is integral with the tab at 372, horizontally spaced from 370b, the tab being relieved at horizontal slits 373 along the edge lengths of 370a, providing for greater or enhanced bending movement of the arm 370, as during penetration of the projection 321 into bone tissue. Projection 321 is integral with the vertical extent 370b of the arm. Projections 322 are carried and formed as in FIGS. 23–27.

The clips as referred to above are metallic, and preferably consist essentially of one of the following:
  i) titanium
  ii) titanium alloy
  iii) an alloy consisting essentially of titanium, aluminum and vanadium
  iv) an alloy consisting essentially of:
    about 90% by weight of titanium
    about 6% by weight of aluminum
    about 4% by weight of vanadium.

What is claimed is:

1. A clip to inter-connect primary and secondary bone zones having edges, comprising in combination:
   a) a tab to extend over and generally parallel to a surface of the secondary bone zone, and above a first level defined by that surface, and
   b) a first projection configured to penetrate the primary bone zone at the edge thereof, and below said first level,
   c) there being an extension of the tab projecting below said first level, said extension carrying the first projection,
   d) said extension including a movable arcuate arm portion.

2. The combination of claim 1 including an extension of the tab projecting below said first level, said extension carrying the first projection.

3. The combination of claim 2 including a second projection carried by the tab and configured to engage the secondary bone zone at the edge thereof, and below said surface level.

4. The combination of claim 3 wherein the second projection is carried by the tab extension.

5. The combination of claim 2 wherein said tab has the form of a plate that extends forwardly and downwardly to define said extension, said extension having S configuration, said first projection extending forwardly from a part of the tab extension below said level.

6. The combination of claim 1 wherein said first projection has a sharp terminal to enable penetration of bone marrow.

7. The combination of claim 3 wherein said first projection projects in a direction generally away from said second projection.

8. The combination of claim 4 wherein said second projection has a sharp terminal to enable penetration of diploe.

9. The combination of claim 5 wherein said second projection extends at an acute angle relative to a rearwardly convex portion of said S-configuration extension, and toward said tab.

10. The combination of claim 2 including at least one of the following: i) a through hole in the tab to receive a fastener, and ii) a through hole in the extension, to receive a fastener.

11. The combination of claim 3 including another second projection carried by the tab in sidewardly spaced relation to the first mentioned second projection, and configured to engage the secondary bone zone at the edge thereof, and below said level.

12. The combination of claim 11 wherein each said second projection has a sharp terminal to enable penetration of bone tissue, said sharp terminals being relatively divergent.

13. The combination of claim 12 wherein each second projection extends back upwardly at an acute angle toward the tab.

14. The combination of claim 3 including said primary bone zone penetrated by a tip of said first projection, and said secondary bone zone engaged by a tip of said second projection.

15. The combination of claim 1 including a cranial bone flap defining said primary bone zone.

16. The combination of claim 15 including multiple of said clips having said first projections penetrating the primary bone zone below a surface defined by the flap.

17. The combination of claim 3 wherein said second projection includes a barb.

18. The combination of claim 17 wherein there are two of said barbs angled upwardly, and located on zones defined by said tab extension, said zones projecting laterally oppositely relative to said first projection.

19. The combination of claim 18 including attachment wings defined by said extension.

20. The combination of claim 1 including a bowed flange integral with the tab.

21. The combination of claim 20 wherein the flange has sections at least one of which is bowed.

22. The combination of claim 21 wherein one of the sections is integral with the tab and the other of the sections is integral with the projection.

23. The combination of claim 22 wherein the first projection extends generally forwardly, and said one section is bowed in said forward direction.

24. The combination of claim 21 wherein the flange has S-configuration.

25. The combination of claim 1 including an S-configuration flange integral with the tab.

26. The combination of claim 25 wherein the flange is also integral with the first projection.

27. The combination of claim 25 including a second projection integral with the S-configuration flange and configured to engage the secondary bone zone at the edge thereof, and below said surface level.

28. The combination of claim 27 wherein the first projection has a sharp terminal to enable penetration of bone marrow, the first projection projecting in a direction generally away from the second projection.

29. The combination of claim 27 wherein said second projection extends generally away from the first projection and is carried by a bowed portion of said S-configuration flange.

30. The combination of claim 27 including another second projection carried by the tab in sidewardly spaced relation to the first mentioned second projection, and configured to engage the secondary bone zone at the edge thereof, and below said level.

31. The combination of claim 30 wherein each said second projection has a sharp terminal to enable penetration of bone tissue, said sharp terminals being relatively divergent.

32. The combination of claim 27 including said primary bone zone penetrated by a tip of said first projection, and said secondary bone zone engaged by a tip of said second projection.

33. The combination of claim 25 including a cranial bone flap defining said primary bone zone.

34. The combination of claim 33 including multiple of said clips having said first projections penetrating the primary bone zone below a surface defined by the flap.

35. The combination of claim 1 wherein the clip consists essentially of one of the following:
   i) titanium
   ii) titanium alloy
   iii) an alloy consisting essentially of titanium, aluminum and vanadium
   iv) an alloy consisting essentially of:
      about 90% by weight of titanium
      about 6% by weight of aluminum
      about 4% by weight of vanadium.

36. The combination of claim 2 wherein said tab includes an arm portion extending in the direction of said projection, and carrying said extension of the tab that projects below said first level.

37. The method of using a clip to interconnect primary and secondary bone zones having edges, the clip comprising
   a) a tab to extend over and generally parallel to a surface of the secondary bone zone, and above a level defined by that surface, and
   b) a first projection carried by the tab and configured to penetrate the primary bone zone at the edge thereof, and below said first level, said method including the steps
      i) advancing the first projection to penetrate said primary bone zone,
      ii) and locating the tab to extend over said surface of the secondary bone zone, and attaching the tab to said surfaces
   c) there being an extension of the tab projecting below said first level, said extension carrying the first projection,
   d) said extension including a movable arcuate arm portion.

38. The method of claim 37 including a second projection carried by the tab and configured to engage the secondary bone zone at the edge thereof, and below said surface level, the method including displacing the clip and said second projection to engage the secondary bone zone at the edge thereof, below said surface level.

39. The method of claim 37 wherein said step i) includes pushing the clip toward said primary bone zone to effect push-in penetration of the first projection into said primary bone zone.

40. The method of claim 39 including orienting the second projection at the edge of the secondary bone zone to resist reverse displacement of the clip in an upward or opposite direction relative to the secondary bone zone.

41. The method of claim 40 including effecting penetration of the edge of the secondary bone zone by the second projection in an angular direction toward the tab.

42. The method of claim 37 including providing an S-configuration flange integral with the tab.

43. The method of claim 42 including providing a second projection integral with the S-configuration flange and configured to engage the secondary bone zone at the edge thereof, and below said surface level.

44. The method of claim 42 wherein said step i) includes pushing the clip toward said primary bone zone to effect push-in penetration of the first projection into said primary bone zone.

45. The method of claim 42 including orienting the second projection at the edge of the secondary bone zone to resist reverse displacement of the clip in an upward or opposite direction relative to the secondary bone zone.

46. The method of claim 45 including effecting penetration of the edge of the secondary bone zone by the second projection in an angular direction toward the tab.

47. A cranial clip comprising, in combination
   a) a clip having a support plate,
   b) a flange integral with the plate and extending away from the plate, the flange having bowed configuration,
   c) at least one push-in tang integral with and protruding from the flange and extending generally parallel to the plate, in spaced relation to the plate,
   d) said tang having a sharp tip to be pushed into cranial soft bone tissue proximate an edge of the cranium,
   e) there being an extension of the flange projecting below said first level, said extension carrying the first projection,
   f) said extension including a movable arcuate portion.

48. The combination of claim 47 including an installation tool removably interfitting the clip, for forwardly pushing and guiding the clip, as the tang penetrates said soft bone tissue.

49. The combination of claim 47 wherein the clip flange has at least one integral ring, and an aligner on the ring.

50. The combination of claim 48 wherein the tool has at least one alignment bar projecting forwardly at the level of the top plate, for guided engagement with the top of the skull.

51. A clip having a tab to surface engage one section of bone, two projections to respectively engage edge portions of two bone sections, and an S-shaped flange integral with the tab and at least one of the projections.

52. The combination of claim 7 wherein the first projection has barbs thereon spaced apart in said directions.

53. A clip to inter-connect primary and secondary bone zones having edges, comprising in combination:
   a) a tab to extend over and generally parallel to a surface of the secondary bone zone, and above a first level defined by that surface,
   b) a first projection carried by the tab and configured to penetrate the primary bone zone at the edge thereof, and below said first level,
   c) and including an extension of the tab projecting below said first level, said extension carrying the first projection,
   d) and wherein said extension has an arm movable relative to the tab, the first projection carried by that arm.

54. The combination of claim 53 including a second projection carried by the tab and configured to engage the secondary bone zone at the edge thereof, and below said surface.

55. The combination of claim 54 wherein the second projection is carried by a part of the extension, relative to which the arm is movable.

56. The combination of claim 53 wherein the arm has S-configuration.

57. Apparatus to prevent a bone fragment from entering the cranial cavity, during positioning of said fragment at an opening in the cranium, comprising
 a) a carrier for the bone fragment, and
 b) an aligner on the carrier to engage a surface or surfaces of the cranium during positioning of the bone fragment relative to said cranial opening,
 c) the carrier including:
  i) a tab to extend over and generally parallel to a surface of the cranium, and above a first level defined by that surface, and
  ii) a first projection configured to penetrate the cranium at the edge thereof, and below said first level,
  iii) there being an extension of the tab projecting below said first level, said extension carrying the first projection,
  iii) said extension including a movable arcuate arm portion.

58. The apparatus of claim 57 wherein the aligner has left and right slide surfaces to engage the cranial outer surface, as the aligner and bone fragment are moved forwardly.

* * * * *